(12) United States Patent
White Gray (10) Patent No.: US 6,617,166 B2
(45) Date of Patent: Sep. 9, 2003

(54) MEASUREMENT OF ACCELERATED WHOLE BLOOD CLOTTING TIME

(75) Inventor: Charles Richardson White Gray, Sussex (GB)

(73) Assignee: Prophylaxis Limited, West Sussex (GB)

( * ) Notice: Subject to any disclaimer, the term of this patent is extended or adjusted under 35 U.S.C. 154(b) by 0 days.

(21) Appl. No.: 09/907,280

(22) Filed: Jul. 17, 2001

(65) Prior Publication Data

US 2002/0106805 A1 Aug. 8, 2002

Related U.S. Application Data

(62) Division of application No. PCT/GB00/00170, filed on Jan. 24, 2000.

(30) Foreign Application Priority Data

Jan. 22, 1999 (GB) .............................................. 9901504

(51) Int. Cl.$^7$ ............................................... G01N 33/86
(52) U.S. Cl. ........................... 436/69; 435/13; 600/369; 73/64.41
(58) Field of Search ............................. 436/69; 435/13; 422/73; 600/369; 73/64.41

(56) References Cited

U.S. PATENT DOCUMENTS

| | | | |
|---|---|---|---|
| 4,814,247 A | | 3/1989 | Spillert et al. ................ 436/69 |
| 5,602,037 A | * | 2/1997 | Ostgaard et al. ............. 422/101 |
| 5,709,889 A | * | 1/1998 | Speck ......................... 424/529 |
| 6,245,573 B1 | * | 6/2001 | Spillert ......................... 422/61 |
| 6,391,568 B1 | * | 5/2002 | Schneider et al. .............. 435/2 |

OTHER PUBLICATIONS

Stenbjerg et al., "Evaluation of the activated whole blood clotting time (ACT) in vitro," *Scan J. Haematol*, 23(3), pp. 239–244 (1979).

Forman et al., "A simplified method for monitoring heparin therapy at the bedside: the activated whole blood clotting time" *American Journal of Hematology*, 11, pp. 277–281 (1981).

Congdon et al., "Monitoring heparin therapy in hemodialysis," *J. Am. Med. Assoc.*, 226, No. 13, pp. 1529–1533 (1973).

Mockros et al., "Anticoagulant kinetics following bolus injection of heparin," *Thrombos. Haemostas.*, 42, pp. 1248–1260 (1979).

Stenbjerg et al., "Heparin concentraitons correlated to the activated whole blood clotting time (ACT) during extracorporeal circulation," *Thrombus. Haemostas.*, 46, pp. 236 (1981) abstract.

* cited by examiner

*Primary Examiner*—Maureen M. Wallenhorst
(74) *Attorney, Agent, or Firm*—Marshall, Gerstein & Borun (57) ABSTRACT

Disclosed is The method of in vitro testing of the state of the blood coagulation system. The Accelerated Whole Blood Clotting Time (A. W. B. C. T.) reflects the degree of over or under activity of the coagulation system of the blood.

13 Claims, 9 Drawing Sheets

Accelerated Whole Blood Clotting Time

FIG. 6

Accelerated Whole Blood Clotting Time

RCCWB with Aspirin added and stimulated by saline or a range of concentrations of collagen

♦ Asp 80 µg/ml   ▫ Asp 40 µg/ml   △ Aspirin 20 µg/ml
⊗ Asp 10 µg/ml   ✳ Control

MEASUREMENT OF ACCELERATED WHOLE BLOOD CLOTTING TIME

This application is a continuation of International Application No. PCT/GB00/00170, filed Jan. 24, 2000, the entire disclosure of which is incorporated herein by reference.

The present invention relates to assessing the degree of over or under activity of the coagulation system, and thus to monitoring patients on anti-coagulant therapy, and to screening patients to predict the degree of a patient's propensity to suffer a thrombosis, such as deep vein thrombosis, pulmonary embolism, coronary thrombosis, strokes, familial thrombophilia, overweight middle aged men, women taking contraceptive pills, diabetics, patients suffering renal failure and the like, as well as the state of the coagulation system as a whole.

The manifestation of cardiovascular disease in the form of coronaries and strokes is the major cause of death or disability in the Western world. Consequently great efforts have been made to discover the causes of cardiovascular disease and to identify risk factors in the hope of identifying vulnerable members of the population with a view to taking preventive action.

Surprisingly although tests have been devised to measure a number of risk factors, there is no commercially available test of coagulation which reflects the net effect of the interaction of all these factors on the coagulation system as a whole in the context of the conditions likely to precipitate a thrombosis.

The present invention is based on the discovery that adenosine diphosphate (ADP) secreted by platelets and bound to their surface receptors, is the physiological thromboplastin.

According to the present invention there is provided a method of in vitro screening of a patient, which comprises measuring the accelerated whole blood clotting time and assessing the degree of over or underactivity of the coagulation system. Thus, the present invention relies on accelerated whole blood clotting time (AWBCT) to enable assessment of the risk of thrombosis.

In order that the invention may be more readily understood, and so that further features thereof may be appreciated, the invention will now be described, by way of example, with reference to the accompanying drawings in which.

Figure 1:
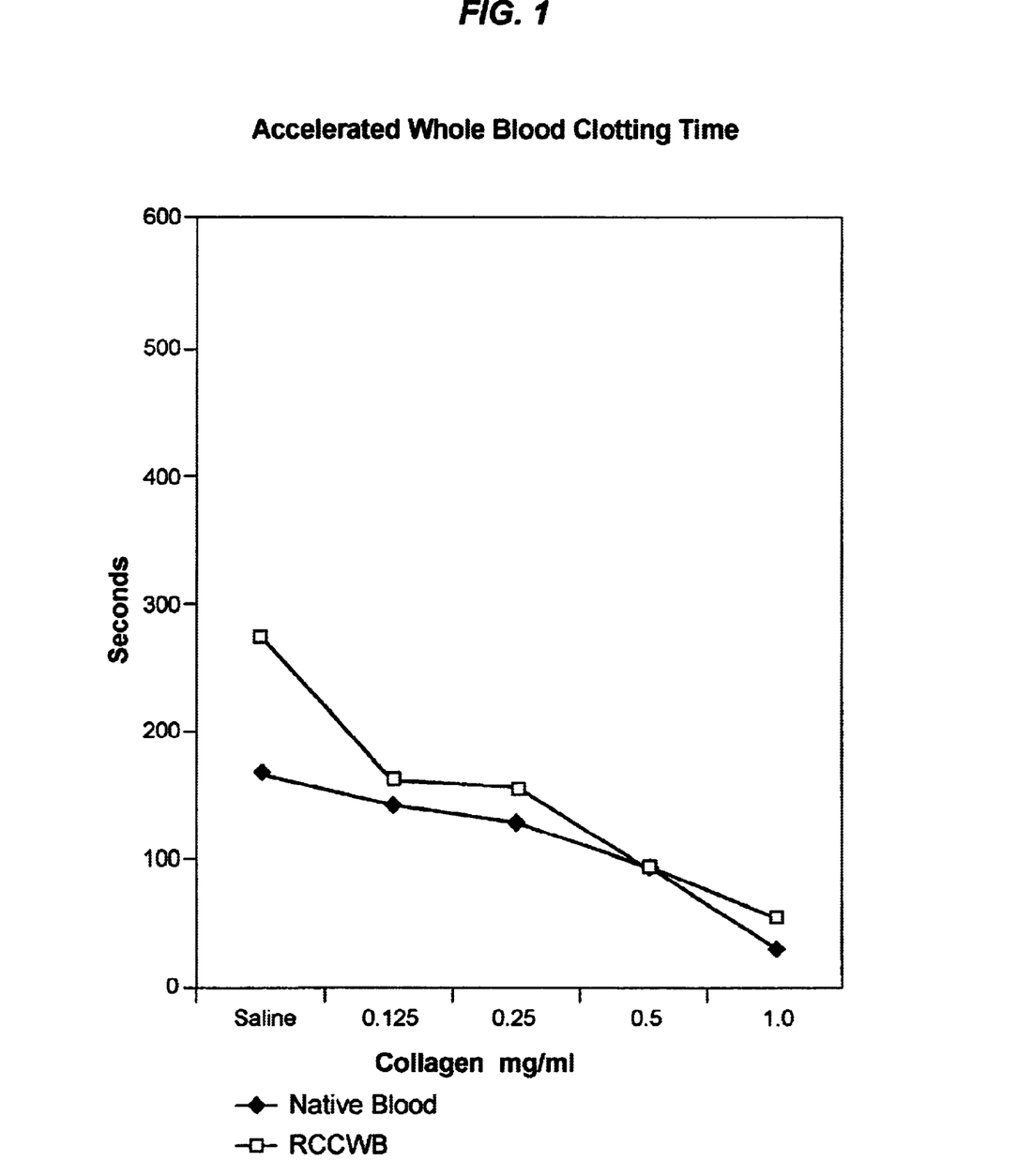
FIG. 1 is a graph showing accelerated whole blood clotting time (AWBCT) results for samples of native blood and recalcified citrated whole blood (RCCWB).
Figure 2:
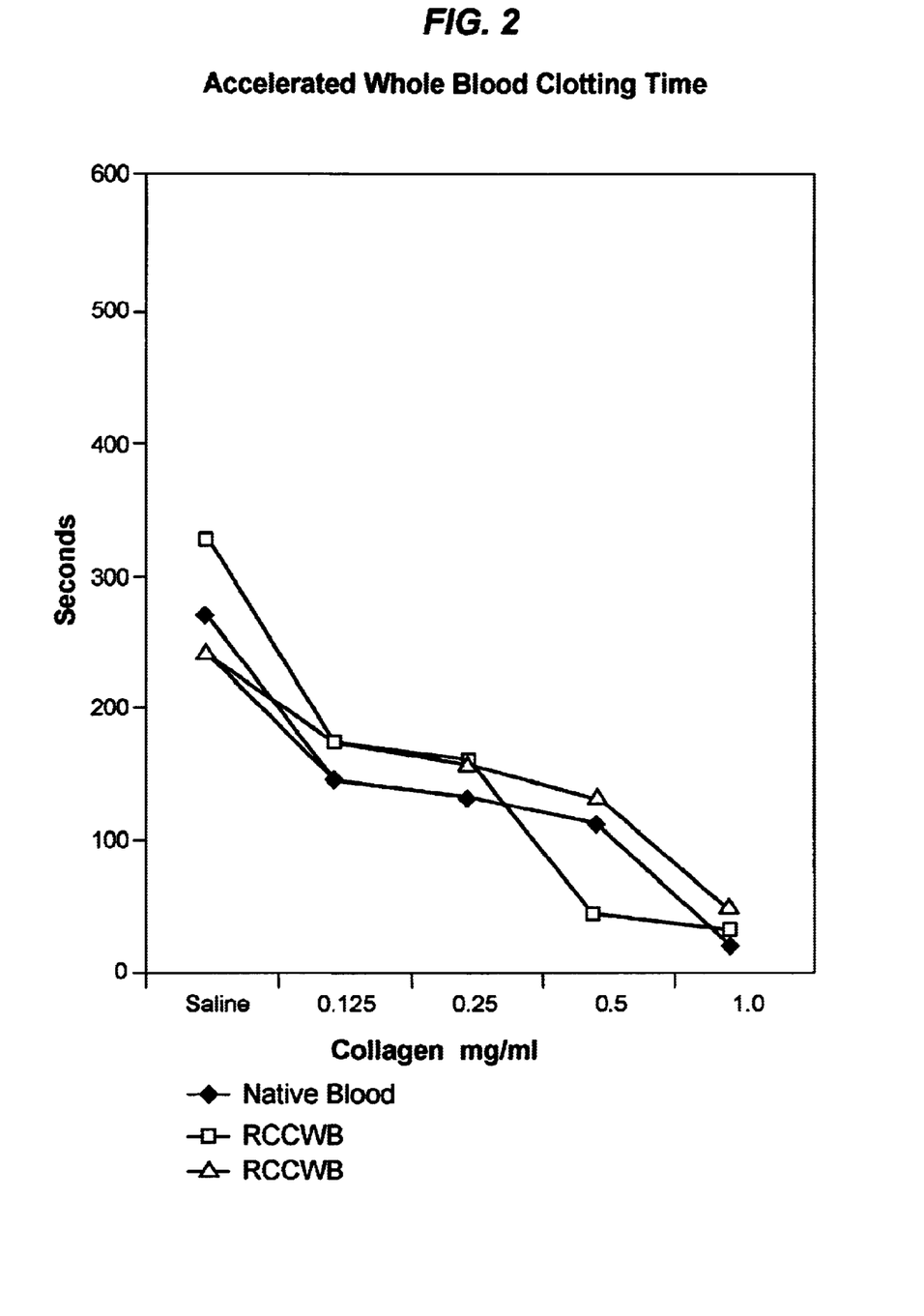
FIG. 2 is a graph showing the AWBCT results for samples of native blood and RCCWB.
Figure 3:
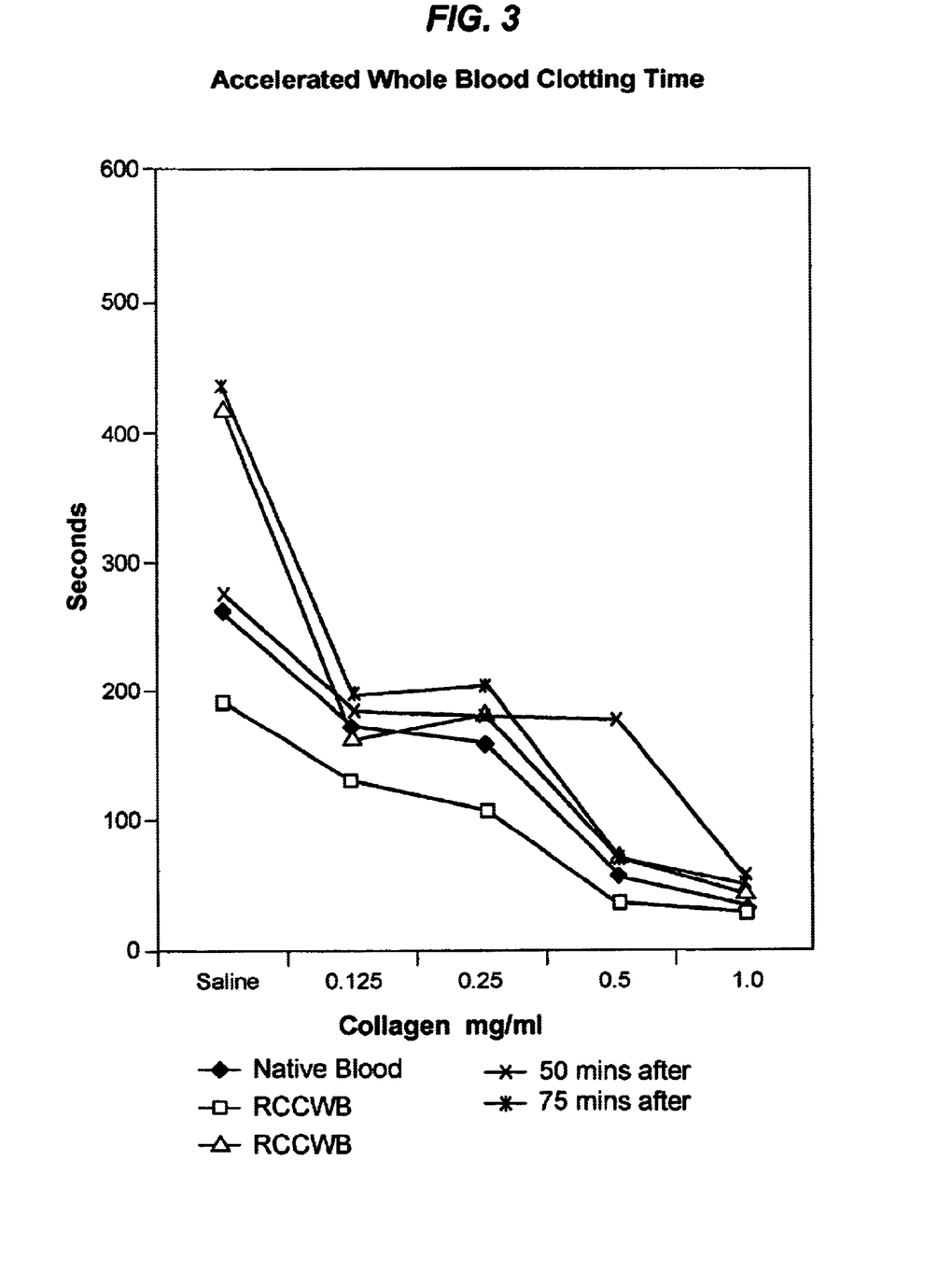
FIG. 3 is a graph showing the AWBCT results for samples of native blood and RCCWB, with the test conducted at intervals after the blood was collected.
Figure 4:
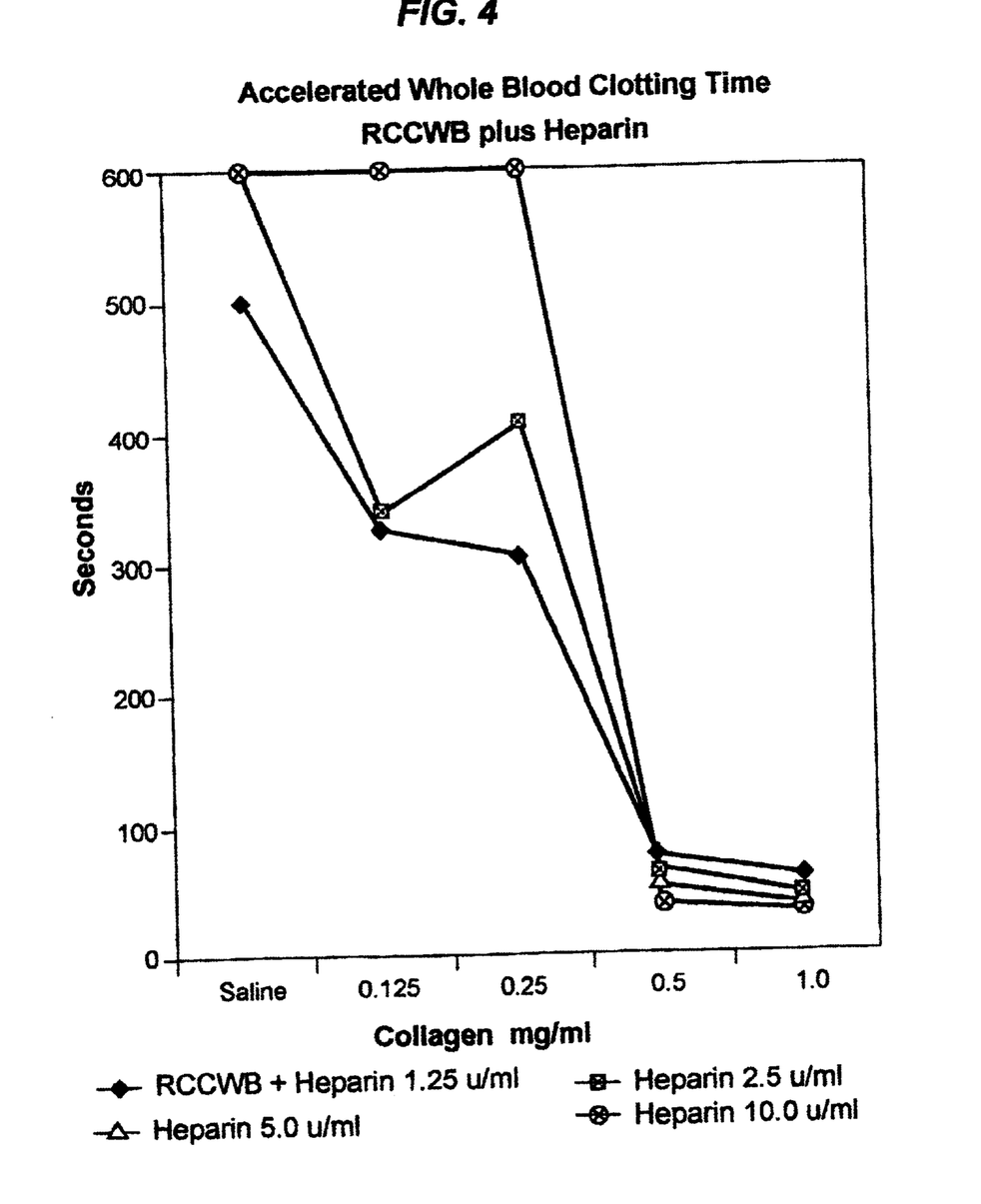
FIG. 4 is a graph showing the AWBCT results for samples of RCCWB spiked with a range of concentrations of unfractionated Heparin
Figure 5:
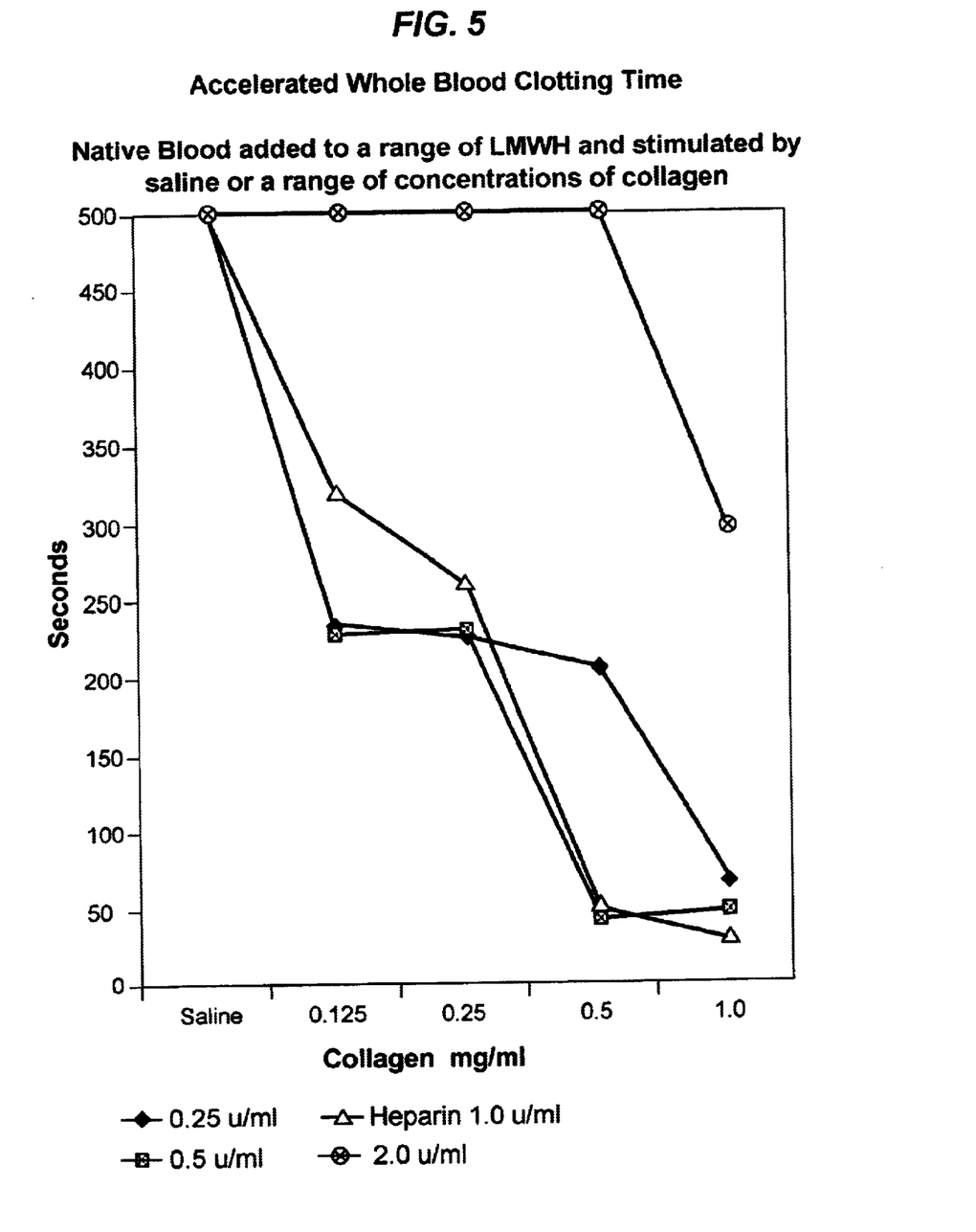
FIG. 5 is a graph showing the AWBCT results for samples of native blood added to a range of concentrations of low molecular weight heparin (LMWH).
Figure 6:
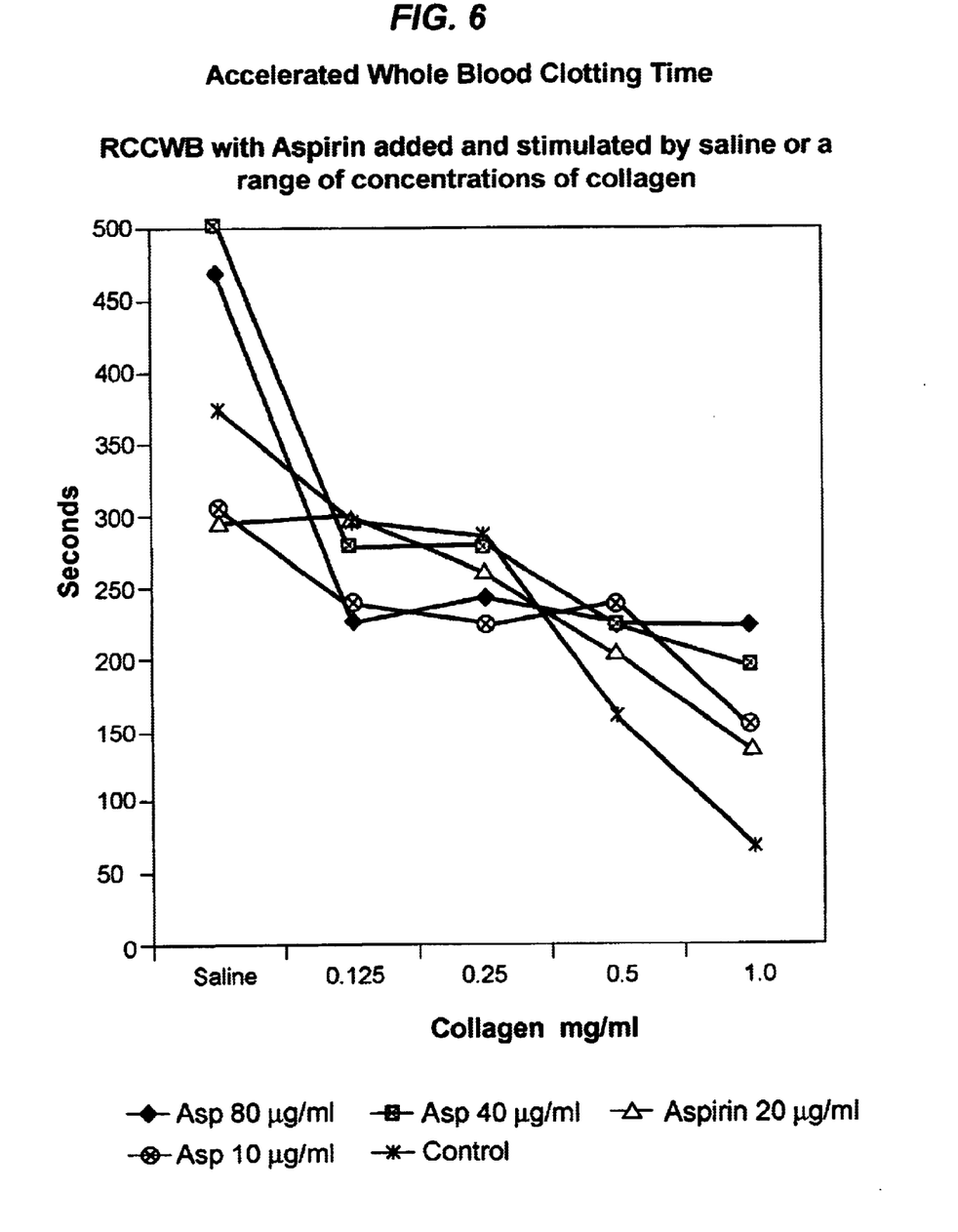
FIG. 6 is a graph showing the AWBCT results for samples of RCCWB spiked with a range of concentrations of Aspirin.
Figure 7:
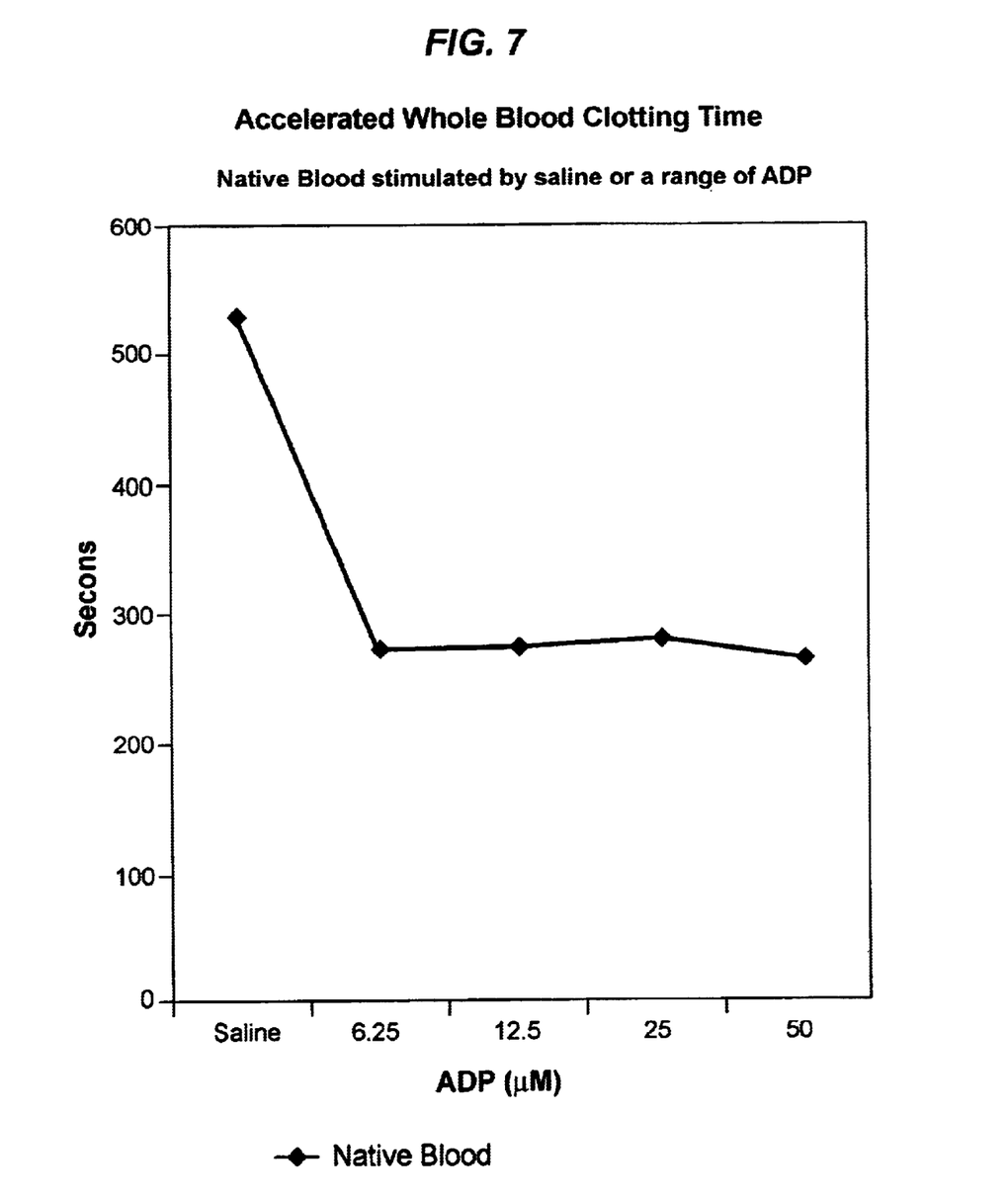
FIG. 7 is a graph showing the AWBCT results for samples of native blood added to a range of concentrations of ADP.
Figure 8:
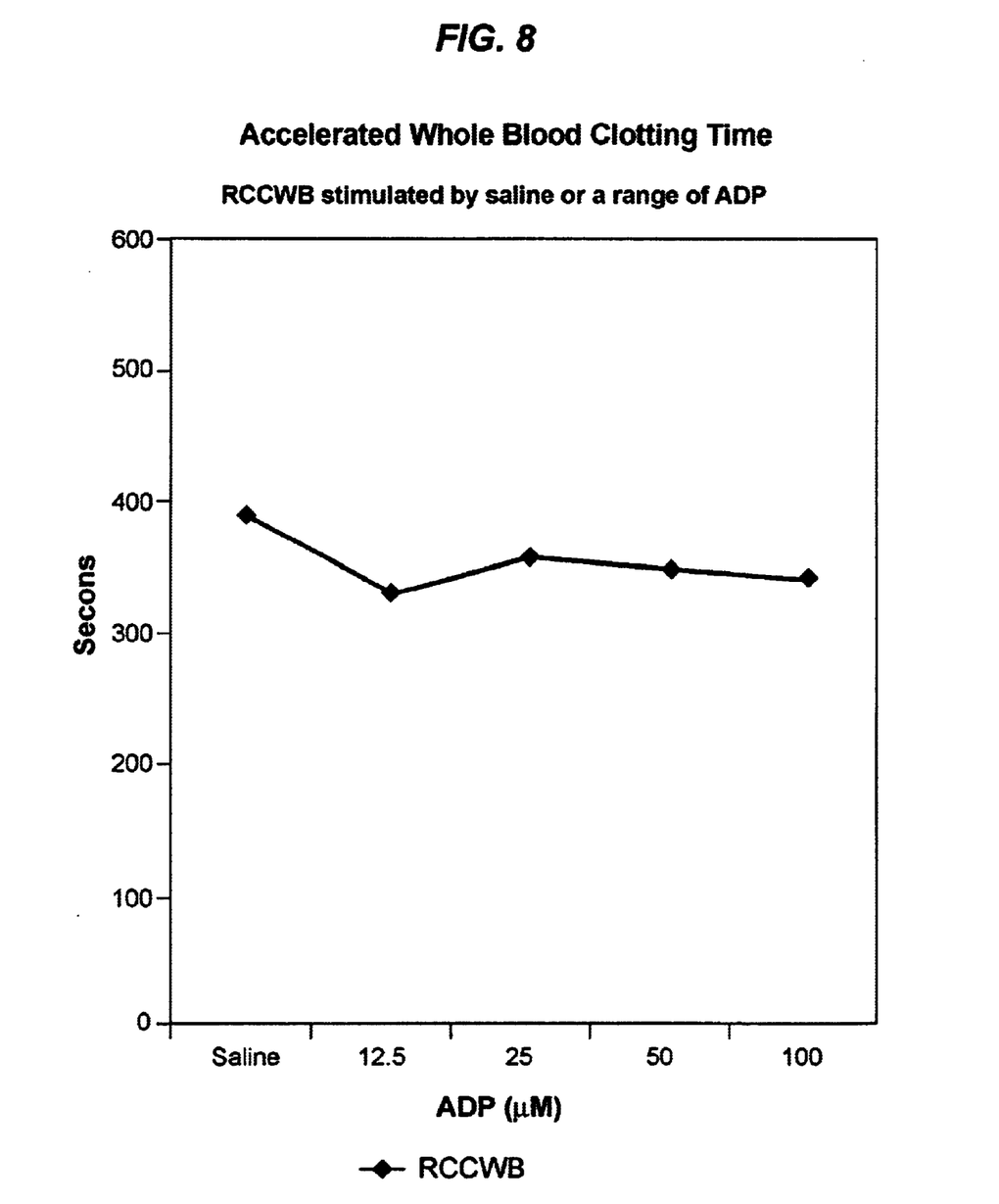
FIG. 8 is a graph showing the AWBCT results for RCCWB spiked with a range of concentrations of ADP.
Figure 9:
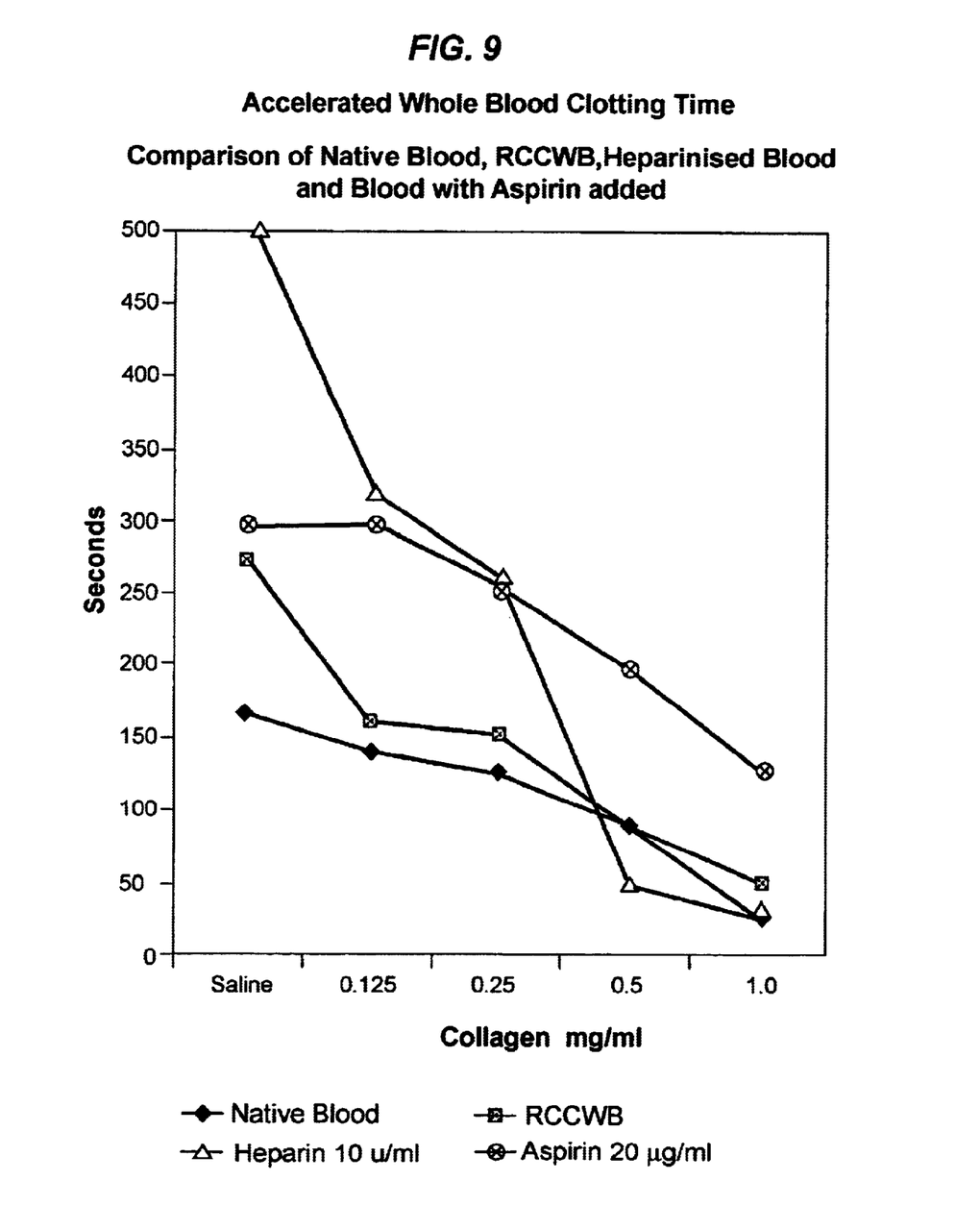
FIG. 9 is a graph showing the AWBCT results for samples of native blood and RCCWB spiked with heparin and aspirin.

Disorders (over activity) of the coagulation system are normally treated with three drugs; aspirin, warfarin or heparin, or combinations of these. There is no clinically test acceptable to monitor treatment with asprin; the prothrombin time (PT) has limited success in controlling treatment with warfarin and is not effective in controlling treatment with heparin.

The PT and accelerated partial thromboplastin time (APTT) were based on the assumption that coagulation involved the interaction of a cascade of plasma proteins (coagulation factors) so deliberately did not attempt to reflect the contribution of the cells, and so did not reflect any contribution from the number and activity of platelets.

The presumed contribution of platelets was provided by thrombosplastin or rabbit brain thromboplastin or platelet sustitute. AWBCT reflects all factors in the blood affecting coagulation, in particular ADP, whether due to secretion from the dense bodies of platelets or secreted from the adrenal medulla or absorbed from the diet.

The test is superior to the prothrombin time (PT, APTT) for the following reasons;

1. The test is performed on whole blood so all factors which affect coagulation will be reflected in the result.
2. The stimulants used are physiological so will simulate physiological/pathological events.
3. The stimulants may interact with both platelets and directly with prothlombin as happens during a cardiovascular event.
4. It has a wider scope than the PT.

Scope of Test

Aspirin

Aspirin inhibits the reactivity of platelets. The stimulants all stimulate platelets which in turn initiate coagulation. The method of testing will reflect in a proportionate way the degree of inhibition of platelets and so of coagulation. This will permit optimisation of the dose and monitoring of the ongoing effect of treatment.

Currently, there is no clinically acceptable test to monitor the risk associated with prophylactic treatment with aspirin, although it has been established that the risk outweighs the benefits in patients with no known cardiovascular problems.

The use of AWBCT provides an assay which will help identify a very low dose aspirin regime which will reduce the risk in patients with no established cardiovascular problems.

Warfarin

The PT was designed specifically to control treatment with warfarin. It was based on the four factor theory of Morrawitch. This proposed that coagulation involved prothrombin, fibrinogen, calcium and thromboplastin. Warfarin prevented the carboxylation of the glutamic acid residues of prothrombin rendering it inactive. The effect was dose dependent. Fibrinogen is rarely a significant problem. The anticoagulation effect of sodium citrate is presumed to be reversed by addition of 25 mM calcium chloride. Extracts of the brain, placenta or tissue factor act as thromboplastin. It was therefore assumed that as three of the four factors were arranged to be present in excess, the coagulation time would reflect the degree of inactivation of prothrombin. The test has proved largely successful in controlliing oral anticoagulant therapy. However, about 20% of patients apparently well controlled as judged by the PT suffer a recurrent thrombosis. It is apparent that the PT does not reflect the degree of contribution of the platelets (platelet count and activity) which if over active or increased in number will strongly augment the coagulation system (under activity or reduced numbers will give a risk of bleeding). It is anticipated that the use of AWBCT will be superior to the PT as it will reflect all the factors in the blood which influence coagulation.

Cardio Vascular Disease

Atheroma and narrowing of the arteries is a predisposing factor for coronary thrombosis or strokes. However, only a small percentage of patients with atheroma actually suffer either. It is therefore assumed that overactivity of the coagulation system in conjunction with atheroma is the dangerous combination.

Coagulation is initiated when ADP (secreted by platelets and bound to the platelet surface) converts prothrombin to thrombin. When the vascular endothelium is breached the platelets are activated, aggregate, form a platelet plug, iniate coagulation and haemostasis is achieved.

However, platelets are also activated when an atheromatous plaque ruptures to expose collagen, when the adrenal glands secret adrenalin and nucleotides in response to stress, when homocysteine (and adenosine) concentrations are elevated, and following a meal rich in nucleotides.

If the platelet sensitivity to these stimuli is increased due to abnormal blood lipids or other factors, coagulation will be initiated leading to coronary thrombosis, stroke, or deep vein thrombosis.

The use of AWBCT aims to simulate the conditions causing the pathological (inappropriate) activation of coagulation and so identify patients with overactive coagulation systems who need treatment.

Haemophilia

The test will also be used to measure the effect of the ratio of nucleotides to nucleotidases in the diet on the state of the coagulation system, as this may have a bearing on the incidence of spontaneous bleeding episodes. A high ratio may protect a low ratio may provoke a bleeding episode. It is known that excessive alcohol which depresses platelets activity may initiate a bleeding episode in haemophiliacs. In haemophilia, where the problem is failure to respond to the number and situations of spontaneous bleeds, the key test may be response of the AWBCT to low intensity stimuli, such as synovial fluid.

In contrast, patients, who have had a coronary) vein bypass operation, or a heart valve replacement, the relevant stimulators to guide anti-coagulation therapy may be more powerful. The intermediate situation of a middle aged man, at risk of having a coronary or stroke the critical stimulators to the coagulation system may only emerged after studies involving the whole range of concentrations and contributions of the patho/physiological agonists.

AWBCT test is based on the discovery that ADP (alone or bound to the surface of platelets) converts prothromnbin to thrombin, in the absence of other factors;

Therefore the state of activity of the coagulation system will depend on four factors;

1. The number and state of the platelets. This is influenced by many factors; disease, haematocrit blood lipids etc. and by treatment with antiplatelet drugs such as aspirn.
2. Prothrombin concentration, and capacity to be converted to thrombin may be inhibited by treatment with warfarin.
3. Thrombin activity which may be blocked by treatment with heparin.
4. Fibrinogen; This is rarely abnormal but the concentration can be reduced by drugs, for example ARVIN (ANCROD).

The use of AWBCT will reflect the state of all these variables and will therefore have the ability to monitor treatment of patients on warfarin, heparin, aspirin and other anti-platelet drugs. In addition, on the assumption that an acute thrombotic event is triggered by stimulation of platelets by rupture of an atheromatous plaque, secretion of adrenaline, and ADP by the adrenals in response to stress, or increased blood nucleotides after a meal rich in nucleotides the test will reflect the over or under response to these patho/physiological stimuli, and so help to identify patients at high risk who need prophylactic treatment.

When the system is neither over or under sensitive, tests on normal volunteers using a range of concentrations of platelet activation factor (PAF), collagen, ADP, adrenaline and/or thrombin will accelerate (shorten) the clotting time of whole blood as compared to a saline control. This will establish the optimal concentrations and combinations of the stimulants to produce maximal acceleration and minimal acceleration. As volunteers may have varying degrees of risk factors such as age, sex, smoking, B.P., lipid profile, the tests in normal volunteers will also give some insight into how these factors affect the pattern of the different stimulants.

When the system is over active, the AWBCT will be shorter than control subjects, either absolutely or as a percentage of the saline control OR the concentration of stimulant required to cause a particular shortening will be less. Probably both will occur and experience will determine which is the more useful indicator.

When the system is inhibited, the AWBCT will be prolonged as compared to normal subjects either absolutely or as a proportion of the saline control OR the concentration of the stimulants to cause a particular shortening will be greater.

The original concept of the AWBCT was to use native blood as this is the most certain way to ensure that prothrombin is in its native conformation but addition of calcium chloride appears to reverse the interaction of citrate with prothrombin, so that it is possible to use citrated blood.

Comparison of the results using native blood and citrated blood was made. 9 parts of citrated blood was added to 1 part calcium n chloride 133 mM, mixed and aliquotes of the recalcified citrated blood added to the wells of the coagulometer containing duplicates of saline control and dilutions of collagen. A concentration of 33 mM calcium chloride is considered to be optimal; but concentrations in the range of, for example, 110–140 mM may be used. However, it should be noted that the length and un-reliability of coagulation times increase with concentrations further from the optimum, especially with higher values.

A copy of the results is given in Table 1. The acceleration with recalcified citrated blood is not as satisfactory as that with native blood. The possibility to use recalcified citrated blood means that blood can be taken into citrate from volunteers or patients and many tests performed on a single sample. Recalcified citrated blood may give acceptable results, if tested soon after blood collection.

Whilst native blood is tested immediately after collection, for example, within two minutes, citrated blood may be stored for a longer period, before being recalcified immediately before the test is conducted. The interval between blood collection and testing may be on the order of one hour. It should be noted that shorter collection intervals give more reliable results.

While there is good reason to test several stimulants at this stage it may well be that dilutions of collagen will suffice for some or all patient groups.

The test is performed on native freshly drawn venous blood, or recalcified citrated blood or heparinised blood.

100 μL of saline control or a range of concentration of a platelet agonists are added to the wells of a coagulometer and then 200 μL of native or RCCWB whole blood added and the coagulation time recorded. The potential agonists are; collagen, ADP, adrenalin, platelet activating factor, thrombin. It is anticipated that the agonist appropriate for specific roles will emerge in the course of clinical studies.

The present invention is demonstrated to work in the test set out hereinafter, with the results shown in tabular as well as graphic from (see the drawings; in the legend thereto, as well as in the Tables RCCWB stands for recalcified citrated whole blood. LMWH stands for Low Molecular Weight Heparin.)

Numbers are the time to coagulation in seconds. The results given are the averages of duplicates, unless otherwise indicated by an asterix, (corresponding to single coagulation times where spurious results have not been averaged).

Reported coagulation times of 500+ or 600+ indicates that coagulation had not occurred after 500 or 600 seconds respectively, with the test then being aborted.

TABLE 1

|  | Saline | Collagen (mg/ml) | | | |
|---|---|---|---|---|---|
|  |  | 1.0 | 0.5 | 0.25 | 0.125 |
| Native Blood | 167 | 24 | 91 | 125 | 140 |
| RCCWB | 273 | 49 | 88 | 151 | 159 |
| Native Blood | 272 | 29 | 118 | 137 | 149 |
| RCCWB | 330 | 39 | 49* | 165 | 177 |
|  | 244 | 56 | 137 | 161* | 178 |
| Native Blood | 269 | 34 | 57* | 162 | 178 |
|  | 199 | 28* | 36 | 111 | 134 |
| RCCWB | 428 | 44 | 71 | 185 | 166 |
| 50 mins later | 284 | 55 | 181 | 184 | 190 |
| 75 mins later | 449 | 50 | 70 | 209 | 202 |
| RCCWB +Heparin 1.25 u/ml | 500+ | 54 | 71 | 302 | 325* |
| RCCWB + Heparin 2.5 u/ml | 600+ | 41 | 61 | 405 | 340 |
| Heparin 5.0 u/ml | 600+ | 31 | 48 | 600+ | 600+ |
| Heparin 10 u/ml | 600+ | 27 | 34 | 600+ | 600+ |

The time interval between collection of blood and testing is indicated in the left hand column.

TABLE 2

Heparinised blood (native blood added to a range of LMWH) and stimulated by saline or a range of concentrations of collagen.

| Heparin | Saline | Collagen (mg/ml) | | | |
|---|---|---|---|---|---|
|  |  | 1.0 | 0.5 | 0.25 | 0.125 |
| 0.25 u/ml | 500+ | 64 | 204* | 224 | 233 |
| 0.5 u/ml | 500+ | 46 | 41 | 228 | 226 |
| 1.0 u/ml | 500+ | 27* | 48* | 259 | 318 |
| 2.0 u/ml | 500+ | 295 | 500+ | 500+ | 500+ |

TABLE 3

Recalcified citrated whole citrated blood with a range of concentrations of aspirin added and stimulated by saline or a range of concentrations of collagen

| Aspirin | Saline | Collagen (mg/ml) | | | | Collection Interval |
|---|---|---|---|---|---|---|
|  |  | 1.0 | 0.5 | 0.25 | 0.125 |  |
| 80 μg/ml | 468 | 212 | 218* | 236 | 224 | +106 min |
| 40 μg/ml | 500 | 184 | 216 | 274 | 275 | +135 min |

TABLE 4

Native blood added to saline or range of ADP

|  | ADP (μM) | | | |
|---|---|---|---|---|
| Saline | 50 | 25 | 12.5 | 6.25 |
| 525 | 255 | 272 | 269 | 265 |

TABLE 5

Recalcified whole blood added to range of ADP

|  | ADP (μM) | | | | Collection Interval |
|---|---|---|---|---|---|
| Saline | 100 | 50 | 25 | 12.5 |  |
| 389 | 341 | 348 | 358 | 329 | +65 mins |

The AWBCT test is superior to any existing test because it reflects the actual contribution to coagulation of platelets, prothrombin, thrombin and fibrinogen, and is not distorted by the use of an artificial platelet substitute. The test will be effective as a screening test to predict the degree of a patients propensity to suffer a thrombosis. This may be relevant in groups known to be at risk such as; familial thombophilia middle aged men, women on the contraceptive pill, diabetic, and renal failure.

The test will also be effective in monitoring the effect of warfarin, heparin aspirin, adenine, or other therapeutic agents by indicating the degree of inhibition of coagulation of the blood as a whole and will be useful in demonstrating the importance of the ratio of nucleotides to nucleotidases in the diet and the value of modifying this by additives or otherwise. In addition, the test may be used to measure the effect of other constituents of the diet such as alcohol, fats, proteins or carbohydrates etc. on the coagulation system and the test may also prove useful in the management of haemophilia by measuring the effect of diet (with high or low ratios of nucleotides to nucleotidases) on the coagulation system and the resultant incidence of spontaneous bleeds. The test should also assist in optimising the dose and frequency of treatment with prophylactic Factor VIII.

The present invention is based on the fact that the AWBCT test will take into account that the state of the coagulation system of a patient will dependent on four factors, all of which can vary for a variety of reasons:
  platelets;
  prothrombin;
  thrombin;
  fibrinogen.

The test is performed on whole blood so that the contribution of all four factors is reflected in the clotting time (including all factors in the blood which influence the function of the four factors)

A range of concentrations and combinations of physiological platelet agonists are added to whole blood and the clotting time recorded.

The test monitors all forms of anticoagulant therapy. It also reflects the degree of over or under sensitivity of the coagulation system as a whole and the graded response to patho/physiological stimuli. Over activity would indicate an individuals risk of suffering a coronary or stroke. Under activity would indicate the risk of suffering a bleeding event. The test demonstrates that the clotting time is proportionate to the strength of the stimulus of the platelets.

It should be noted that although the AWBCT has been described above as using a conventional coagulometer, it is to be understood that the tests may be performed using alternative devices. For example, the AWBCT may be performed using cards coated with different concentrations and combinations of agonists, to be inserted into a corresponding coagulometer. Such cards may, for example, be coated with a wide range of different concentrations and combinations of agonists. With references to haemophiliacs, such a system may not only be used to monitor the effect of diet, but may also prove useful in the monitoring of the appropriate dose in the frequency of administration of factor VIII.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A method of in vitro screening and/or monitoring of a whole blood clotting time of a patient comprising the steps of:
   a. collecting a whole blood sample from the patient;
   b. adding one or more physiological/pathological platelet agonists exclusively either to the whole blood sample within two minutes of collection or to a citrated whole blood sample from the patient recalcified immediately prior to addition of the one or more platelet agonists, and
   c. measuring the whole blood clotting time of the whole blood sample, wherein a degree of an overactive or underactive coagulation system is assessed.

2. The method according to claim 1 wherein the measurement of the whole blood clotting time further comprises a measurement of a whole blood clotting time in the absence of the one or more physiological/pathological agonists, to act as a baseline control.

3. The method according to claim 1 wherein the one or more physiological/pathological agonists is selected from the group consisting of collagen, adenosine diphosphate, adrenalin, platelet activation factor, thrombin, and synovial fluid.

4. The method according to claim 1 wherein the measurement of the whole blood clotting time is performed using a range of concentrations of the one or more physiological/pathological agonists.

5. A method of monitoring patients on an anticoagulant therapy comprising the steps of:
   a. collecting a whole blood sample from the patient;
   b. adding one or more physiological/pathological platelet agonists exclusively either to the whole blood sample within two minutes of collection or to a citrated whole blood sample from the patient recalcified immediately prior to addition of the one or more platelet agonists; and
   c. measuring a whole blood clotting time of the whole blood sample, wherein a degree of an overactive coagulation system due to the anticoagulant therapy is assessed.

6. The method of claim 5, wherein the anticoagulant therapy comprises a low dose aspirin prophylactic regime.

7. The method of claim 5, wherein the anticoagulant therapy comprises an administration of warfarin.

8. The method of claim 5, wherein the anticoagulant therapy comprises an administration of heparin.

9. A method of identifying patients with overactive coagulation systems comprising the steps of:
   a. collecting a whole blood sample from the patient;
   b. adding one or more physiological/pathological platelet agonists exclusively either to the whole blood sample within two minutes of collection or to a citrated whole blood sample from the patient recalcified immediately prior to addition of the one or more platelet agonists; and
   c. measuring a whole blood clotting time of the whole blood sample, wherein a degree of an overactive coagulation system is assessed.

10. A method of measuring an effect of a diet on a coagulation system of a patient suffering from haemophilia comprising the steps of:
    a. collecting a whole blood sample from the patient;
    b. adding one or more physiological/pathological platelet agonists exclusively either to the whole blood sample within two minutes of collection or to a citrated whole blood sample from the patient recalcified immediately prior to addition of the one or more platelet agonists; and
    c. measuring a whole blood clotting time of the whole blood sample, wherein a degree of an underactive coagulation system due to the diet of the patient is assessed.

11. A method of monitoring the acute or prophylactic treatment of Haemophilia with Factor VIII in a patient comprising the steps of:
    a. collecting a whole blood sample from the patient;
    b. adding one or more physiological/pathological platelet agonists exclusively either to the whole blood sample within two minutes of collection or to a citrated whole blood sample from the patient recalcified immediately prior to addition of the one or more platelet agonists; and
    c. measuring a whole blood clotting time of the whole blood sample, wherein a degree of an underactive coagulation system due to the acute or prophylactic treatment of Haemophilia with Factor VIII in the patient is assessed.

12. A method of assessing a degree of risk of suffering a thrombosis in a patient comprising the steps of:
    a. collecting a whole blood sample from the patient;
    adding one or more physiological/pathological platelet agonists exclusively either to the whole blood sample within two minutes of collection or to a citrated whole blood sample from the sample recalcified immediately prior to addition of the one or more platelet agonists; and
    c. measuring a whole blood clotting time of the whole blood sample, wherein a degree of an overactive coagulation system, indicating a risk of suffering a thrombosis in the patient, is assessed.

13. A method of measuring an effect of smoking on a whole blood clotting time of a patient comprising the steps of:
   a. collecting a whole blood sample from the patient;
   b. adding one or more physiological/pathological platelet agonists exclusively either to the whole blood within two minutes of collection or to a citrated whole blood sample from the patient recalcified immediately prior to addition of the one or more platelet agonists; and
   c. measuring a whole blood clotting time of the whole blood sample, wherein a degree of an overactive coagulation system due to smoking by the patient is assessed.

* * * * *

UNITED STATES PATENT AND TRADEMARK OFFICE
CERTIFICATE OF CORRECTION

PATENT NO. : 6,617,166 B1  Page 1 of 1
APPLICATION NO. : 09/907280
DATED : September 9, 2003
INVENTOR(S) : Charles Richardson White Gray It is certified that error appears in the above-identified patent and that said Letters Patent is hereby corrected as shown below:

Column 7, line 46, "agonists," should be -- agonists; --

Column 8, line 63, "from the sample" should be -- from the patient --

Column 9, line 8, "whole blood within" should be -- whole blood sample within --

Signed and Sealed this

Fourteenth Day of November, 2006

JON W. DUDAS
*Director of the United States Patent and Trademark Office*